United States Patent
Nistor

(10) Patent No.: US 7,180,054 B2
(45) Date of Patent: Feb. 20, 2007

(54) METHODS AND DEVICES FOR ERASING ERRORS AND COMPENSATING INTERFERENCE SIGNALS CAUSED BY GAMMAGRAPHY IN RADIOMETRIC MEASURING SYSTEMS

(75) Inventor: Alecsandru Nistor, Grenzach (DE)

(73) Assignee: Endress+Hauser GmbH+Co. KG, Maulburg (DE)

(*) Notice: Subject to any disclaimer, the term of this patent is extended or adjusted under 35 U.S.C. 154(b) by 177 days.

(21) Appl. No.: 10/498,509

(22) PCT Filed: Dec. 11, 2002

(86) PCT No.: PCT/EP02/14083

§ 371 (c)(1),
(2), (4) Date: Feb. 10, 2005

(87) PCT Pub. No.: WO03/052396

PCT Pub. Date: Jun. 26, 2003

(65) Prior Publication Data

US 2005/0116157 A1    Jun. 2, 2005

(30) Foreign Application Priority Data

Dec. 19, 2001  (DE) ............................ 101 62 703

(51) Int. Cl.
G01F 23/284 (2006.01)
G01N 9/24 (2006.01)
(52) U.S. Cl. .................. 250/252.1; 250/339.04
(58) Field of Classification Search .......... 250/252.1, 250/352, 339.03, 339.04, 370.15
See application file for complete search history.

(56) References Cited

U.S. PATENT DOCUMENTS 5,218,202 A    6/1993  Evers
6,515,285 B1 *  2/2003  Marshall et al. ............ 250/352

FOREIGN PATENT DOCUMENTS

| DE | 42 33 278 A1 | 4/1994 |
| DE | 44 05 238 A1 | 8/1995 |
| DE | 197 22 549 A1 | 12/1998 |
| DE | 199 23 688 A1 | 11/2000 |
| GB | 2 327 128 A | 1/1999 |

* cited by examiner

Primary Examiner—Otilia Gabor
(74) Attorney, Agent, or Firm—Bacon & Thomas, PLLC

(57) ABSTRACT

A method and device for the error-blanking and -compensation of interference signals caused by gammagraphy in radiometric measuring systems for process measurements. The device includes, an input for measured values $Lm_{(t)}$ of a process variable $L_{(t)}$ measured by the detector, an input for at least one, non-radiometrically measured and likewise monitored, first process parameter $P_1=P_{1(t-\tau)}$, whose change leads with delay by a possible delay time $\tau k$, which can also be $\tau k=0$, to a change $\Delta Lm=Lm_{(t)}-Lm_{(o+1)}$ of the radiometric, measured value $Lm_{(t)}$; an output, which is connected to a process control system, and an evaluation- and error-compensation facility, which determines during operation the change $\Delta Lm=Lm_{(u)}-Lm_{(n+1)}$ of the radiometric, measured values $Lm_{(n)}$ und $Lm_{(n+1)}$ registered by the detector at two, arbitrary per se, times $t_i$ and $t_{i+1}$ following one after the other, and, by means of the calculative relationship $\Delta Lm=f(\Delta P_1)$, compares such with a change $\Delta P_1=P_{1(n+1-r)}$ of the first, non-radiometrically measured process parameter in the corresponding time interval.

15 Claims, 5 Drawing Sheets

METHODS AND DEVICES FOR ERASING ERRORS AND COMPENSATING INTERFERENCE SIGNALS CAUSED BY GAMMAGRAPHY IN RADIOMETRIC MEASURING SYSTEMS

FIELD OF THE INVENTION

The invention relates to methods and devices for error-blanking and error-compensation of interference signals brought-about by gammagraphy in radiometric measuring systems.

BACKGROUND OF THE INVENTION

Radiometric measuring systems have served for many years as contactless measuring methods for process measurements. They are applied where process parameters, such as e.g. fill level of a medium in a container, an interface and/or a density of the medium, have to be measured under difficult conditions, such as e.g. extreme temperatures and pressures. Known radiometric measuring systems include, typically, a radioactive radiator and a detector attached at, or on, a container or pipe, as well as also including an evaluation unit. Measuring methods associated therewith are likewise known per se. Especially in the chemicals industry, radiometric measurements are indispensable for difficult processes.

On the other hand, exactly in the plants of the chemical industry, the integrity of pipes and containers and their connections is very important and, therefore, must be examined from time to time. In the context of a non-destructive, materials testing of pipelines, weld seams and pressure vessels, gammagraphy is frequently applied, in the measuring methods of which, radioactive radiators and detectors are likewise used. When such a gammagraphy measurement is performed in proximity to a radiometric measuring system, interferences with the radiometric measuring system can arise, stemming from the radioactive radiator used for the gammagraphy, so that errors are introduced into the measurements of the process variables.

In one of the methods commonly used currently, for suppressing interferences from gammagraphy, the affected radiometric measurement in the vicinity of the gammagraphy inspection is stopped, or interrupted, before the gammagraphy is begun, and the last measurement of the process variables is retained, i.e. stored, and, in effect, frozen. During the gammagraphy measurement, the measurement of the process variables is at rest in the radiometric measuring system and is not available for process control. Upon termination of the gammagraphy inspection, the radiometric measuring system is turned on again, and the measurement of the process variables resumed. The disadvantages of this method are evident: Either the process variable registered by the radiometric measuring system can no longer be measured and monitored, and that can lead to serious effects in the process control; or a gammagraphy measurement must be forsaken, thus no inspection of pipe and container walls and weld seams, when no interruption of the registering of process variables is allowable, this being especially the case for radiometric measurements of the fill level of a medium in a container, where pumps are controlled on the basis of the current fill level measurement. The other alternative, of shutting down the affected branch of the process, is likewise problematic for most plant operators.

SUMMARY OF THE INVENTION

The invention, therefore, has as an object the providing of method and device permitting radiometric measurement of a process variable in the face of possible interferences caused by concurrent gammagraphy inspection.

This object is achieved by a method for error-blanking and -compensation of interference signals originating from gammagraphy in a radiometric measuring system, wherein a process variable $L_{(t)}$ is registered by means of a radioactive radiator and a detector, which method includes the following steps:

a) while measurement is occurring, for two, arbitrary per se, times $t_i$ and $t_{i+1}$, following one after the other and defining a time interval, or time period, the change $\Delta Lm = Lm_{(ti)} - Lm_{(ti+1)}$ between two radiometric, measured values $Lm_{(ti)}$ and $Lm_{(ti+1)}$ registered by the detector at these times is determined and, by means of a predetermined, calculative relationship $\Delta Lm = f(\Delta P_i)$, compared with a change $\Delta P_1 = P_{t(n-r)} - P_{t(ti+-r)}$ of a first, non-radiometrically measured process parameter registered in the corresponding time interval;

b) in case the change $\Delta Lm = Lm_{(ti)} - Lm_{(n+1)}$ of the radiometric, measured value $Lm_{(t)}$ corresponds to a previous change $\Delta P_1 = P_{l(ti-\tau)} - P_{l(ti+1-r)}$ of the first, non-radiometrically measured process parameter in the corresponding time interval and to the calculative relationship $\Delta Lm = f(\Delta P_1)$, than it is assumed that no interference of the radiometric measuring system is present, wherein, from the last-measured, radiometric, measured value $Lm_{(n+1)}$, the associated process variable $L_{(n+1)}$ is determined and issued onto a bus connected with a process control system, without an additional signal indicating an interference;

c) in case the change $\Delta Lm = Lm_{(ti)} - Lm_{(ti+1)}$ of the radiometric, measured value $Lm_{(t)}$ does not correspond to a previous change $\Delta P_1 = P_{1(ti-\tau)} - P_{1(ti+1-\tau)}$ of the first, non-radiometrically measured process parameter in the corresponding time interval and to the calculative relationship $\Delta Lm = f(\Delta P_1)$, than it is assumed that an interference of the radiometric measuring system is present, wherein then, based on the previous change $\Delta P_1 = P_{1(ti-\tau)} - P_{1(ti+1-\tau)}$ of the first process parameter $P_1$, a radiometric measurement $Lc_{(t+1)}$ is calculated by means of the recorded, calculative relationship $\Delta Lm = f(\Delta P_1)$ for the time $t_{i+1}$;

wherein, from the calculated, radiometric measurement $Lc_{(ti+1)}$, the associated process variable $\overline{L}_{(ti+1)}$ is determined, and is issued onto the bus connected with the process control system, together with an additional, interference-indicating signal; and wherein, in a subsequent recording at a time $t_{i+2}$ of the change $\Delta P_1 = P_{1(ti+1-\tau)} - P_{1(ti+2-\tau)}$ of the first, non-radiometrically measured process parameter and of the measuring of the radiometric, measured value $Lm_{(n+2)}$, the latter is used together with the calculated radiometric measurement $Lc_{(ti+1)}$ to determine the change $\Delta Lm = Lc_{(ti+1)} - Lm_{(ti+2)}$ and this is referenced corresponding to the steps d), respectively e), for determining whether an interference of the radiometric measuring system is still present.

In a preferred embodiment of the method of the invention, the following steps are performed before start-up of the radiometric measuring system and before commencement of the actual measuring operation:

a) For a measured value $Lm_{(ti)}$ measured by the detector of the radiometric measuring system, at least one, non-radiometrically measured and likewise monitored, first process parameter $P_1 = P_{1(t-\tau)}$ is identified, whose change $\Delta P_1 = P_{1(tj-\tau)} - P_{1(tj+1-\tau)}$ leads, for arbitrary times $t_{j-\tau}$ and $t_{j+1-\tau}$, with delay by a possible delay time $\tau$, which $\tau_1$ which can even be $\tau=0$, to a change $\Delta Lm=Lm_{(tj)}-Lm_{(tj+1)}$ of the radiometric, measured value $Lm_{(t)}$;

b) from changes $\Delta Lm$ of the radiometric, measured value $Lm_{(t)}$ determined at different operating and process conditions and at different times $t_i$ and resulting from changes $\Delta P_1$ of the non-radiometrically measured, first process parameter, a calculative relationship $\Delta Lm=f(\Delta P_1)$ is formulated and stored.

In further development of the method of the invention, it is provided that, prior to issue of the signal indicating the interference of the radiometric measuring system, it is ascertained whether the change $\Delta Lm$ of the radiometric, measured value is smaller than a change $\delta=|\Delta Lm_{max}|$ previously predetermined as maximally allowable; and that only in the case where $\Delta Lm \geqq \delta$ is the signal indicating the interference of the radiometric measurement signal issued onto the bus.

The above-stated object is additionally achieved by a device for error-blanking and -compensation of gammagraphy-caused interference signals in a radiometric measuring system with a radioactive radiator and a detector, which device includes:

an input for measured values $Lm_{(t)}$ of a process variable $L_{(t)}$ measured by the detector, an input for at least one non-radiometrically measured and likewise monitored, first process parameter $P_1=P_{1(t-\tau)}$, whose change leads to a change $\Delta Lm=Lm_{(tj)}-Lm_{(tj+1)}$ of the radiometric, measured value $Lm_{(t)}$ delayed by a possible delay time $\tau k$, which can also be $\tau k=0$;

an output, which is connected with a process control system, and an evaluation and error compensation facility, which determines during operation the change $\Delta Lm=Lm_{(ti)}-Lm_{(ti+1)}$ of the radiometric, measured values $Lm_{(ti)}$ und $Lm_{(ti+1)}$ registered by the detector at two, arbitrary per se, times $t_i$ and $t_{i+1}$ following one after the other, and, by means of the calculative relationship $\Delta Lm=f(\Delta P_1)$, compares such with a change $\Delta P_1=P_{1(ti-\tau)}-P_{1(ti+1-\tau)}$ of the first, non-radiometrically measured process parameter registered in the corresponding time interval;

which, in case the change $\Delta Lm=Lm_{(ti)}-Lm_{(ti+1)}$ of the radiometric, measured value $Lm_{(t)}$ corresponds to a previous change $\Delta P_1=P_{1(ti-\tau)}-P_{1(ti+1-\tau)}$ of the first, non-radiometrically measured process parameter in the corresponding time interval and to a predetermined, calculative relationship $\Delta Lm=f(\Delta P_1)$, determines the associated process variable $L_{(ti+1)}$ from the last measured radiometric, measured value $Lm_{(ti+1)}$ and issues this variable to the output and onto a bus connected with a process control system, without an additional signal indicating an interference;

which, in case the change $\Delta Lm=Lm_{(ti)}-Lm_{(ti+1)}$ of the radiometric, measured value $Lm_{(t)}$ does not correspond to a previous change $\Delta P_1=P_{1(ti-\tau)}-P_{1(ti+-\tau)}$ of the first, non-radiometrically measured process parameter in the corresponding time interval and to a predetermined, calculative relationship $\Delta Lm=f(\Delta P_1)$, recognizes an interference of the radiometric system, wherein then, based on the previous change $\Delta P_1=P_{1(ti-\tau)}-P_{1(ti+-\tau)}$ of the first process parameter $P_1$, a radiometric measurement $Lc_{(i+1)}$ is calculated based on the recorded, calculative relationship $\Delta Lm=f(\Delta P_1)$ for the time $t_{i+1}$;

wherein the associated process variable $L_{(ti+1)}$ is determined from the calculated radiometric measurement $Lc_{(n+1)}$ and this variable is issued, with an additional signal indicating the interference, onto the output and onto the bus connected with the process control system; and wherein in a subsequent registering of the change $\Delta P_1=P_{1(ti+1-\tau)}-P_{1(ti+2-\tau)}$ of the first, non-radiometrically measured process parameter and the measuring of the radiometric, measured value $Lm_{(n+2)}$ occurring at a time $t_{i+2}$, the change $\Delta Lm=Lc_{(ti+1)}-Lm_{(ti+2)}$ is determined from this radiometric, measured value and the calculated radiometric measurement $Lc_{(ti+1)}$, in order to determine whether an interference of the radiometric measuring system is still present.

Other preferred embodiments of the invention concern the measured value $Lm_{(t)}$ measured by the detector of the radiometric system, which measured value can be a measure for a fill level of a medium in a container, a density of such a medium in a container, or an interface of at least two phases of one or more media in a container or pipe.

Other preferred embodiments of the invention concern the first, non-radiometrically measured, process parameter $P_1$, which is:

a pressure in the interior of the container or in a pipe connected with the interior of the container, a temperature in the interior of the container or in a pipe connected with the interior of the container, or a flow rate of a medium in a pipe connected with the interior of the container.

In still other embodiments of the invention, it is provided that a plurality of process parameters $P_k$ for (k=1, 2, . . . ) are monitored, whose change $\Delta P_k=P_{k(ti-\tau k)}$ for arbitrary times $t_{j-\tau k}$ and $t_{j+1-\tau k}$ and delayed by a possible delay time $\tau K$, which can also be $\tau k+0$, leads to a change $\Delta Lm=Lm_{(tj)}-Lm_{(tj+1)}$ of the radiometric, measured value $Lm_{(j)}$;

wherein, on the basis of measurements for different operational and process conditions, a calculative representation of the dependence of the change of the radiometric, measured value $Lm_{(i)}$ on a change of each separate process parameter, or a plurality of the process parameters, $P_k$ is formulated to $\Delta Lm=f(\Delta P_1, \Delta P_2, \ldots )$, and wherein, during operation, it is examined by means of the calculatively recorded relationship $\Delta Lm=f(\Delta P_1, \Delta P_2, \ldots )$, whether an interference of the radiometric measuring system is present.

An advantage of the invention is that safety is not compromised in the process control, since the process variables to be measured can be monitored without interruption. Additionally, the invention offers the possibility for creating a device, with which, in the manner of a retrofit kit, older and already-installed, radiometric measuring systems can be upgraded. Such a retrofit kit is usually to be arranged between the radiometric measuring system and the process control system.

The invention will now be described and explained in greater detail with reference to different embodiments of the invention and on the basis of the accompanying drawings, whose figures show as follows:

DESCRIPTION OF THE PREFERRED EMBODIMENTS

Figure 1:
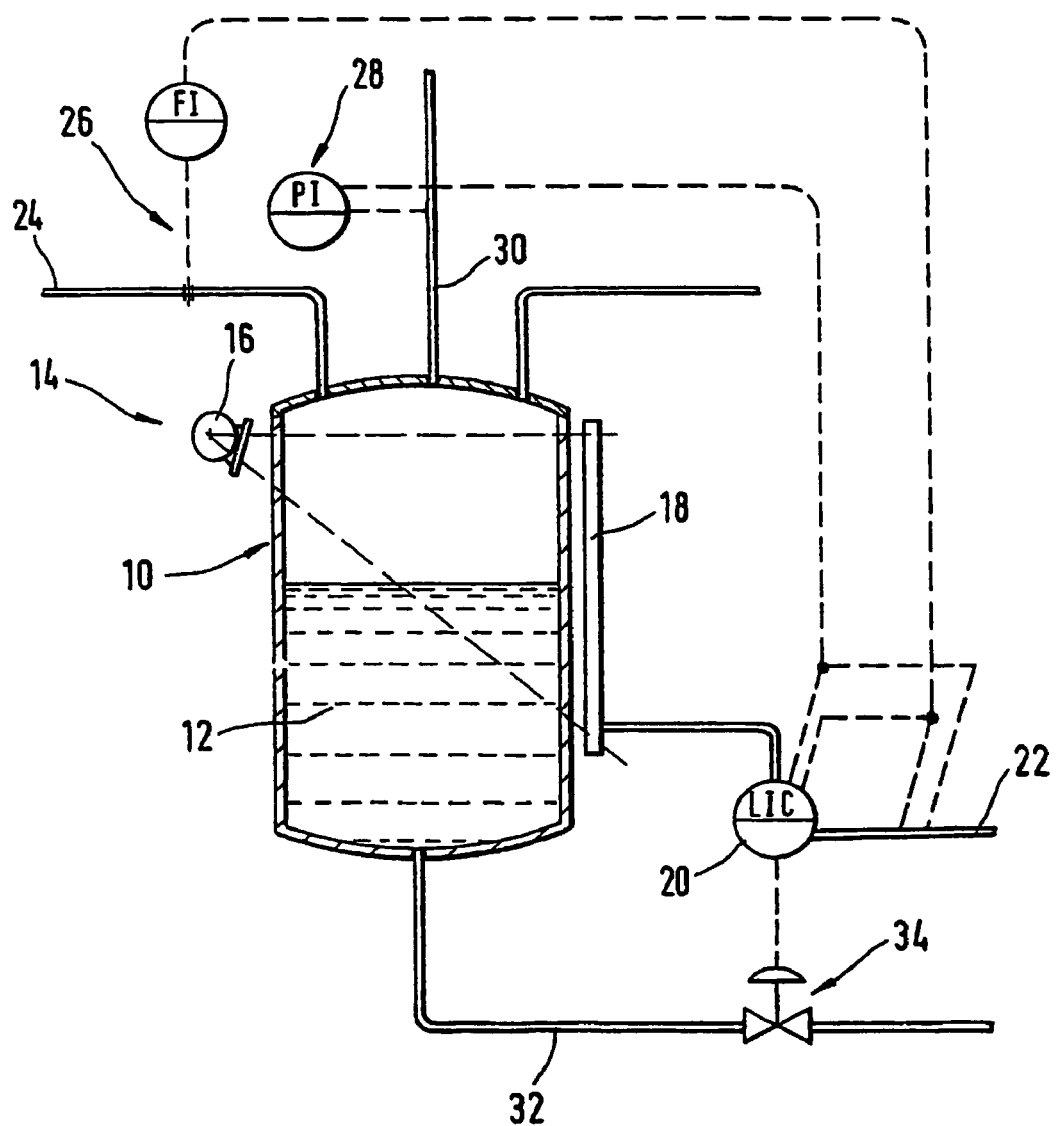
FIG. 1: is a schematic drawing of a part of a process monitored by a radiometric measuring system.

For simplification and clarity, equal elements, components and parts of different embodiments of the invention are provided with equal reference characters.

FIG. 1 shows an example of a part of a conventional industrial plant for a so-called process. Placed at a container 10, which contains a medium 12 in its interior, is a radiometric measuring system 14. System 14 includes a radiator 16 and a detector 18. As shown in FIG. 1, as is usual for such installations, the radioactive radiator 16 and the detector 18 are arranged on opposite sides of the container 10. An area covered by the radiation emitted by the radioactive radiator 16 and striking the detector 18 is indicated by the dashed lines but otherwise not described here in more detail. The radiometric measuring system 14 includes, additionally, an evaluation electronics 20, in which a signal for the registered process variable $L_{(t)}$ is formed from a measured value $Lm_{(t)}$ measured by the detector 18 at an arbitrary time $t_i$. The process variable $L_{(t)}$ here and as discussed further below, is preferably the fill level of the medium 12 in the container 10. In principle, however, it can be any other process variable capturable by a radiometric measuring system, for instance the density of a container or pipe, or an interface between two phases of one or more media in the container or in a pipe.

Frequently, the evaluation electronics 20 is, as shown in FIG. 1, located away from the detector 18 and connected with the same by a cable. It can, however, just as well be situated in the housing of the detector 18, or in a housing in common with such. In most cases, the evaluation electronics 20 is connected with a bus 22, over which the process variables won from the measurement signals are conducted to a process control system (not shown here). However, instead of the bus 22 shown in FIG. 1, it is also possible to use a wireless bus as the connection to the process control system or to a corresponding, central control location.

Besides the radiometric measuring system 14, the example of a process illustrated in FIG. 1 shows other measuring devices, with which non-radiometrically registered process parameters can be determined, which have an influence on the measured value $Lm_{(t)}$, or which are influenced thereby. In short, changes of the process parameters are an indication of possible changes of the process variables.

In, or on, as the case may be, a first pipeline 24, which opens into the container 10 and serves for filling with the medium 12, a flow rate measuring device 26 is installed, with which a flow rate through the pipeline 24 can be registered as a first process parameter $P_1 = P_{1(t)}$ of the medium 12. As a result of the medium 12 flowing through the first pipeline 24 into the container 10, the measured value $Lm_{(t)}$ of the process variable, fill level $L_{(t)}$, changes in the container 10, to the extent that an equal volume of the medium is not flowing out in the same period of time.

Serving for monitoring the pressure in the vapor or gas layer above medium 12 in the container 10 is a pressure measuring device 28, which is placed in or on a second pipeline 30, which opens from above into the interior into the interior of the container 10. With the pressure measuring device, the pressure in the container 10 in the vapor or gas layer above the medium in container 10 is registered as the second process parameter $P_2 = P_{2(t)}$. Changes of the pressure can indicate changes of the fill level $L_{(t)}$ of the medium in the container 10. The particular illustration of the pressure measuring device 28 in FIG. 1 in, or on, as the case may be, the second pipeline 30 is not obligatory and does not represent a limitation of the invention. Those skilled in the art known that the pressure measuring device 28 can also be placed in the container 10 in the area of its lid.

Arranged in a third pipeline 32, which opens into the floor, or sump, as the case may be, of the container 10, is a valve 34, with the help of which the outflow of the medium 12 out of the container 10 can be controlled. The position of the valve 34, or, more accurately, its actual degree of opening, is registered as a third process parameter $P_3 = P_{3(t)}$.

Changes of this third process parameter $P_3$, which indicate an opening or closing of the valve 34 and, therewith, increased, or lessened, or even no, outflow of the medium 12 out of the container 10, lead to a change of the fill level $L_{(t)}$ of the medium in the container 10, in so far as not corresponding inflow of the medium 12 occurs. The inflow is, as above-described, monitored with the flowrate measuring device 26 by way of the change of the first process parameter $P_1$.

Summarizing, it is evident that changes of one or more process parameters $P_1$, $P_2$, $P_3$ indicate a change of the radiometrically registered, measured value $Lm_{(t)}$ of the fill level $L_{(t)}$. A relationship between the changes of the process parameters $P_1$, $P_2$, $P_3$ and a change of the radiometrically registered measured value $Lm_{(t)}$ is recorded, according to the invention, preferably for different operating and process conditions and at different times $t_i$ and $t_{i-30\ 1}$, one following the other, before the actual, regular start-up of a particular plant, or borrowed as a function known from a comparable plant and, if need be, adapted for the present one.

The functional relationship is determined as changes $\Delta Lm$ of the radiometric, measured value $Lm_{(t)}$ due to changes of the process parameters $\Delta P_1$, $\Delta P_2$, $\Delta P_3$, with a calculative relationship $\Delta Lm = f(\Delta P_1, \Delta P_2, \Delta P_3)$ being formulated and stored. In so far as a change of one or more process parameters $P_1$, $P_2$ or $P_3$ leads with delay by a possible delay time $\tau$, which can also be $\tau = 0$, to a change $\Delta Lm = Lm_{(tj)} - Lm_{(tj+1)}$ of the radiometric, measured value $Lm_{(t)}$, this is taken into consideration when determining the calculative relationship $\Delta Lm = Lm_{tj} - Lm_{tj+1} = f(\Delta P_1, \Delta P_2, \Delta P_3)$, with $\Delta P_1 = P_{1(tj-\tau)} - P_{1(tj+1-\tau)}$, $\Delta P_2 = P_{2(tj-\tau)} - P_{2(tj+1-\tau)}$ and $\Delta P_3 = P_{3(tj-\tau)} - P_{3(tj+1-\tau)}$. This calculative relationship $\Delta Lm = Lm_{tj} - Lm_{tj+1} = f(\Delta P_1, \Delta P_2, \Delta P_3)$ is preferably stored in a memory of the evaluation electronics 20 or in a memory attached thereto and is available there for the error-blanking and -compensation of evoked interference signals.

Three process parameters have been chosen for the example of an embodiment shown in FIG. 1 and described here. It is, however, clear for one skilled in the art, that it could, in other plants and under other circumstances, be more process parameters, or less, whose changes lead to changes of the process variables and which are to be monitored and processed according to the invention.

FIG. 1 also indicates connecting lines from the flowrate measuring device 26 and the pressure measuring device 28 to the bus 22. The process parameters measured by the flow rate measuring device 26 and by the pressure measuring device 28 are also fed to the evaluation electronics 20 of the radiometric measuring system 14 for further evaluation and processing.

Figure 2:
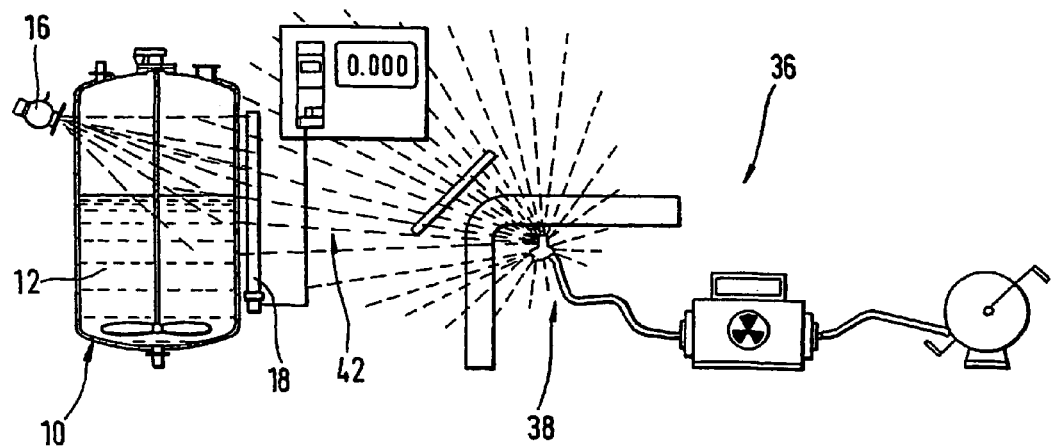
FIG. 2: is a schematic drawing of a part of a process monitored by a radiometric measuring system, with a gammagraphy measuring system operating in its vicinity.

FIG. 2 shows schematically and in simplified manner the container 10 and the radiometric measuring system 14 for determining fill level of the medium 12, together with a gammagraphy measuring system 36, which is being used in the vicinity, in the area of a neighboring pipe bend 38 for its examination. Radioactive radiation emitted there from a radiator 40 and directed onto the tube bend 38 is likewise received by the detector 18 of the radiometric measuring system 14 and interferes with, or corrupts, the measurement signals serving for determining the fill level of the medium 12. This foreign radiation additionally received by the detector 18 leads to the fill level being indicated as less than is really present in the container. This is, however, undesired to the highest degree and dangerous.

Figure 3:
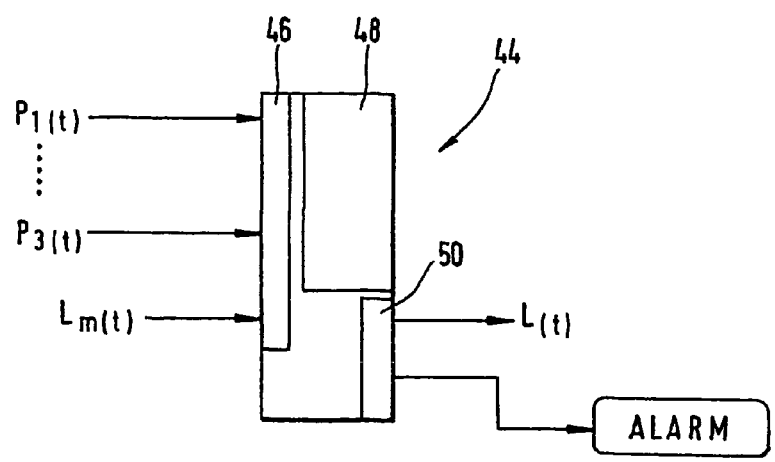
FIG. 3: is a sketch of the principles of a device for evaluating and for error-blanking and -compensation according to the invention.

FIG. 3 shows a sketch of the principles of a device 44 for evaluating and for error-blanking and -compensation according to the invention. This device 44 includes an input 46 for radiometric, measured values $Lm_{(t)}$ measured by the detector 18 and for the further, non-radiometrically measured process parameters $P_1=P_{1(t)}$, $P_2=P_{2(t)}$ and/or $P_3=P_{3(t)}$, an evaluation and error compensation facility 48 in the real sense, as well as an output 50. A power supply naturally needed for the device 44 for the evaluation, error-blanking and -compensation is not shown here, for reasons of simplification and clarity.

When measuring operation is running, the evaluation and error compensation device 48 determines the change $\Delta Lm = Lm_{(ti)} - Lm_{(ti+1)}$ for two radiometric, measured values $Lm_{(ti)}$ and $Lm_{(ti+1)}$ registered by the detector at two, arbitrary per se, times $t_i$ and $t_{i+1}$ and tests by means of the predetermined and stored, calculative relationship $\Delta Lm = f(\Delta P_1, \Delta P_2, \Delta P_3)$ based on the changes $\Delta P_1$, $\Delta P_2$ or $\Delta P_3$ of the process parameters registered in the same time interval, whether an interference of the radiometric measuring system 14 as illustrated in FIG. 2 is present or not. For the case that an interference is assumed, a value for issue for the process variable $L_{(t)}$ is determined in the evaluation and error compensation device 48, using the method described in more detail below for error-blanking and -compensation, and issued, together with a corresponding signal indicating an interference, for example an alarm signal, from output 50 onto the bus 22 (see, in this connection, FIG. 1). For the case that no interference is assumed, a value for issue for the process variable $L_{(t)}$ is determined in the evaluation and error compensation device 48, on the basis of the last measured radiometric, measured value $Lm_{(t)}$, and such value is issued from output 50, without alarm signal, onto the bus 22.

Figure 4:
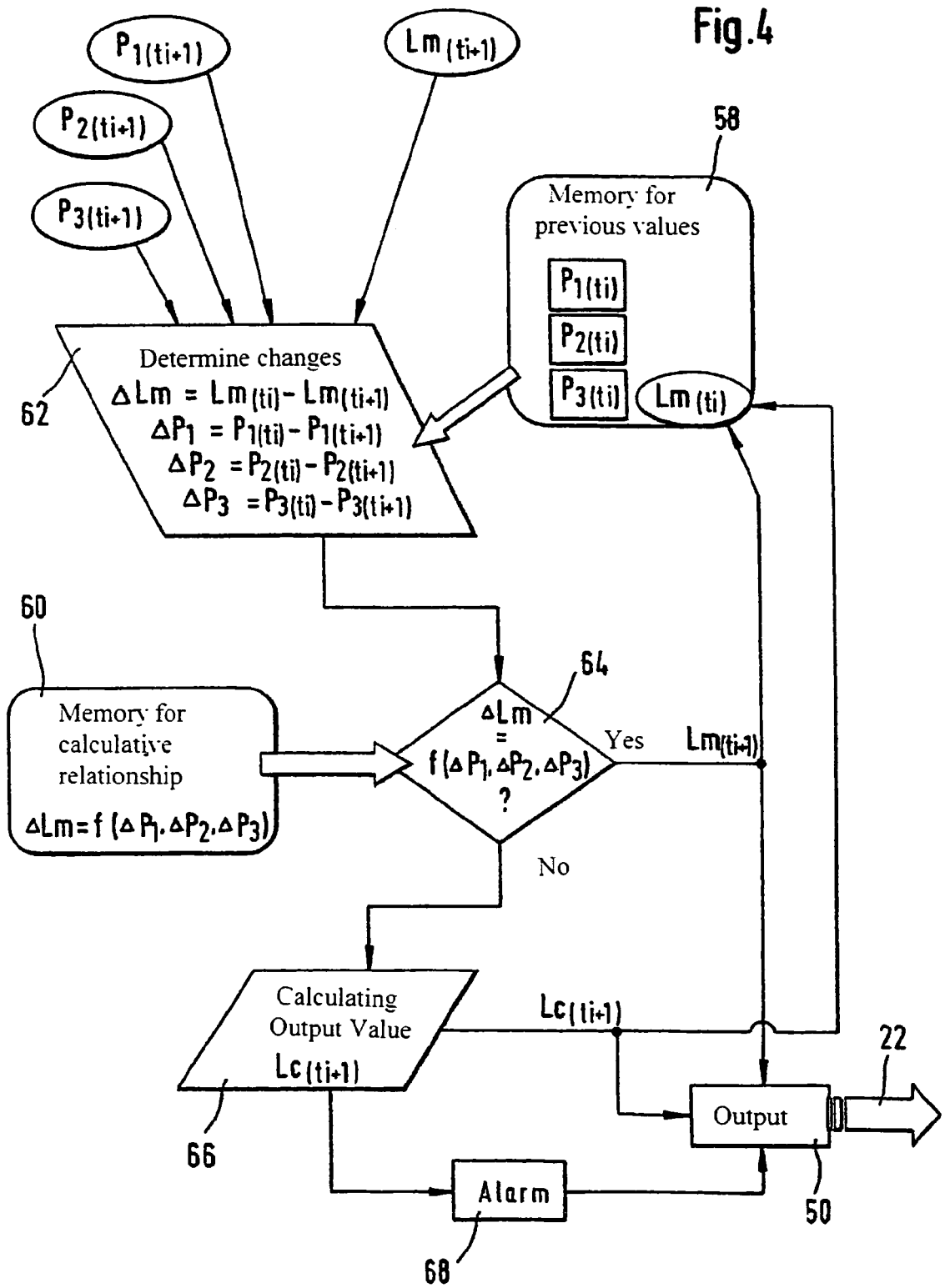
FIG. 4: is a flow diagram of a preferred embodiment of a method for evaluating, error-blanking and -compensation according to the invention.

FIG. 4 illustrates in a flow diagram a preferred first embodiment of a method of the invention for evaluation, error-blanking and -compensation according to the invention. By way of example, a time interval from a running measuring operation is determined by two, arbitrary times $t_i$ and $t_{i+1}$, one following the other. Measured are the radiometric, measured value $Lm_{(t)}$ and a plurality of process parameters. In the example of an embodiment presented here, there are three process parameters $P_1$, $P_2$, $P_3$, which are preferably the process parameters shown in FIG. 1 and described in the description belonging thereto. For simplification, it is assumed that the calculative relationship $\Delta Lm = f(\Delta P_1, P_2, \Delta P_3)$, captured and determined in advance for different operating and process conditions, is already formulated for the further processing and stored in suitable form in a memory 60 of the device for error-blanking 44 (see, in this connection, also FIG. 3). Additionally, it is assumed that, at the time $t_{i+1}$, at which the flow of the method displayed in FIG. 4 begins (anew), the measured values registered at the previous time $t_i$ are likewise stored in suitable form in a memory 58 of the device 44 for error-blanking and are available for a further processing.

After the actually measured values $Lm_{(ti+1)}$, $P_{1(ti+1)}$, $P_{2(ti+1)}$, $P_{3(ti+1)}$ are present in the evaluation electronics 20 (see, in this connection, also FIG. 1), a determination 62 of this changes $\Delta Lm = Lm_{(ti)} - Lm_{(ti+1)}$, $\Delta P_1 = P_{1(ti)} - P_{1(ti+1)}$, $\Delta P_2 = P_{2(ti)} - P_{2(ti+1)}$ und $\Delta P_3 = P_{3(ti)} - P_{3(ti+1)}$ with respect to the values $Lm_{(ti)}$, $P_{1(ti)}$, $P_{2(ti)}$, $P_{3(ti)}$ registered at the preceding time $t_i$ and read out of the memory 58, is executed. Subsequently, a comparison 64 is performed, in which the change of the radiometric, measured value $\Delta Lm = Lm_{(ti)} - Lm_{(ti+1)}$ is compared with the changes $\Delta P_1$, $\Delta P_2$, $\Delta P_3$ of the process parameters registered in the same time interval and in which the calculative relationship $\Delta Lm = f(\Delta P_1, \Delta P_2, \Delta P_3)$ read from the memory 60 is used to test whether the actually measured change $\Delta Lm = Lm_{(ti)} - Lm_{(ti+1)}$ corresponds to a change given by the calculative relationship $\Delta Lm = f(\Delta P_1, \Delta P_2, \Delta P_3)$. The values of the process parameters $P_1$, $P_2$, $P_3$ measured for the time $t_{i+1}$ are loaded into the memory 58 and are available for the next measurement time $t_{i+2}$ for determining the changes $\Delta P_1$, $\Delta P_2$, $\Delta P_3$ for the following time period $t_{i+1}$ to $t_{1+2}$.

In case the actually measured change $\Delta Lm = Lm_{(ti)} - Lm_{(ti-1)}$ of the radiometric, measured value $Lm_{(t)}$ corresponds to the changes $\Delta P_1$, $\Delta P_2$, $\Delta P_3$ of the measured process parameters, it is assumed that no interference of the radiometric measuring system is present. The associated process variable $L_{(ti+1)}$ is determined from the last measured radiometric value $Lm_{(ti+1)}$ and issued onto the bus 22 connected with the process control system, without any additional signal indicating an interference. The radiometric, measured value $Lm_{(ti+1)}$ is loaded in the memory 58 and is available for the following measurement time $t_{1+2}$ as a reference value for determining the change $\Delta Lm$ for the time period $t_{i+1}$ to $t_{i+2}$.

In case the change $\Delta Lm = Lm_{(ti)} - Lm_{(ti+1)}$ of the radiometric, measured value $Lm_{(t)}$ does not correspond to the changes $\Delta P_1$, $\Delta P_2$, $\Delta P_3$ of the nonradiometrically measured process parameters and to the calculative relationship $\Delta Lm = f(\Delta P_1, \Delta P_2, \Delta P_3)$, it is assumed that an interference of the radiometric measuring system is present, for example due to an incursion of foreign radiation from a nearby gammagraphic measuring system (see, in this connection, also FIG. 2. In this case, the known, calculative relationship is used to execute a calculation 66 $\Delta Lm = f(\Delta P_1, \Delta P_2, \Delta P_3)$ for the considered time period $t_i$ to $t_{i+1}$, which delivers a calculated measurement $Lc_{(i+1)}$ for the time $t_{i+1}$. From a practical point of view, this can be done, for example, by using the calculative relationship $\Delta Lm = f(\Delta P_1, \Delta P_2, \Delta P_3)$ to determine a permissible change $\Delta Lc_{(ti,ti+1)}$ for the time period of interest, and then calculating a measurement $Lc_{(ti+1)}$ from $Lc_{(ti+1)} = Lm_{(ti)} + \Delta Lc_{(ti,ti+1)}$. The associated process variable $L_{(ti+1)}$ for the calculated radiometric measurement $Lc_{(ti+1)}$ is next calculated and issued onto the bus 22 connected with the process control system, together with an additional signal 68 indicating an interference. The calculated radiometric measurement $Lc_{(ti+1)}$ is loaded into the memory 58 and is available for the following measurement time $t_{i+2}$ as a reference value for determining the change $\Delta Lm = Lc_{(ti+1)} - Lm_{(ti+2)}$ for a following time period $t_{i+1}$ to $t_{i+2}$.

For a following time $t_{i+2}$ (and also for further times following thereon), the described method of the invention, as illustrated in FIG. 4, proceeds anew, with process parameters $P_{1(ti+2)}$, $P_{2(ti+2)}$, $P_{3(ti+2)}$ registered at the new time taking the place of the process parameters $P_{1(ti+1)}$, $P_{2(ti+1)}$, $P_{3(ti+1)}$ measured at the time $t_{i+1}$. The time-indicating indices of the separate steps of the method are to be adjusted correspondingly. The above-described determination 62 of the change $\Delta P_1$, $\Delta P_2$, $\Delta P_3$ is correspondingly executed for the new time period of interest.

The determination 62 of the change $\Delta Lm$ of the measured value of the process variable for the time period $t_{i+1}$ to $t_{i+2}$ depends on whether an interference of the radiometric measuring system was previously ascertained, or not. If not interference is present, then the method proceeds as described above, for the new time period $t_{i+1}$ to $t_{i+2}$ being considered. For the case of an interference, the calculated radiometric measurement $Lc_{(ti+1)}$ then appears in place of the measured value $Lm_{(ti+1)}$, so that the change $\Delta Lm$ of the radiometric, measured value in the time period from $t_{i+1}$ to $t_{i+2}$ is determined from $\Delta Lm=Lc_{(ti+1)}-Lm_{(ti+2)}$. Should the change $\Delta Lm=Lc_{(ti+1)}-Lm_{(ti+2)}$ for the time period $t_{i+1}$ to $t_{i+2}$ not correspond to the registered changes $\Delta P_1$, $\Delta P_2$, $\Delta P_3$ for the new time period under consideration the known, calculative relationship $\Delta Lm=f(\Delta P_1,\Delta P_2,\Delta P_3)$, then the radiometric measurement $Lc_{(ti+2)}$ for the time $t_{i+2}$ is calculated with the help of the calculative relationship $\Delta Lm=f(\Delta P_1,\Delta P_2,\Delta P_3)$, along with the process variable $L_{(ti+2)}$ belonging thereto, which is then issued onto the output 50, together with the alarm signal 68.

In turn, for each newly considered time, the actually measured process parameters $P_{1(ti+2)}$, $P_{2(ti+2)}$, $P_{3(ti+2)}$ and the value of the process variable, be it as the actually measured value $Lm_{(ti+2)}$ or as the calculated measurement $Lc_{(ti+2)}$, are stored and held ready in the memory 58 for further processing in subsequent measurements.

In the description to this point of the method presented in FIG. 4 for the error-blanking and -compensation of the invention, it has been assumed that, for the time period under consideration, changes of the process parameters $P_1$, $P_2$, $P_3$ appear also immediately in a change of the measured value $Lm$ of the process variable for this time period. In the case, however, where a change of a process parameter P leads with delay by a possible delay time $\tau$, which can also be $\tau=0$, to a change $\Delta Lm=Lm_{(ij)}-Lm_{(ij+1)}$ of the radiometric, measured value $Lm_{(t)}$, then the method of the invention should use the change of the relevant process parameter, for example $\Delta P_1$, for time period of $t_{j-\tau}$ to $t_{j+\tau}$ for $j=1, \ldots, i, i+1, i+2, \ldots$, thus for a time period corrected by the delay time $\tau$, especially then, when the calculate relationship $\Delta Lm=f(\Delta P_1,\Delta P_2,\Delta P_3)$ depends on the particular time period under consideration. Thus, it can, by all means, happen, that, as in the case of the part of a conventional, industrial process plant illustrated in FIG. 1, changes of the process parameter 'flow rate', which are registered with the flow rate measuring device 26, appear delayed by a certain time as a change of the fill level measurement registered with the radiometric measuring system 14.

The method of the invention does not change when the delay time $\tau$ is taken into consideration, only the indices of the method illustrated in FIG. 4 are to be adjusted appropriately. One proceeds in the same way also when the different process parameters have different delay times.

Figure 5:
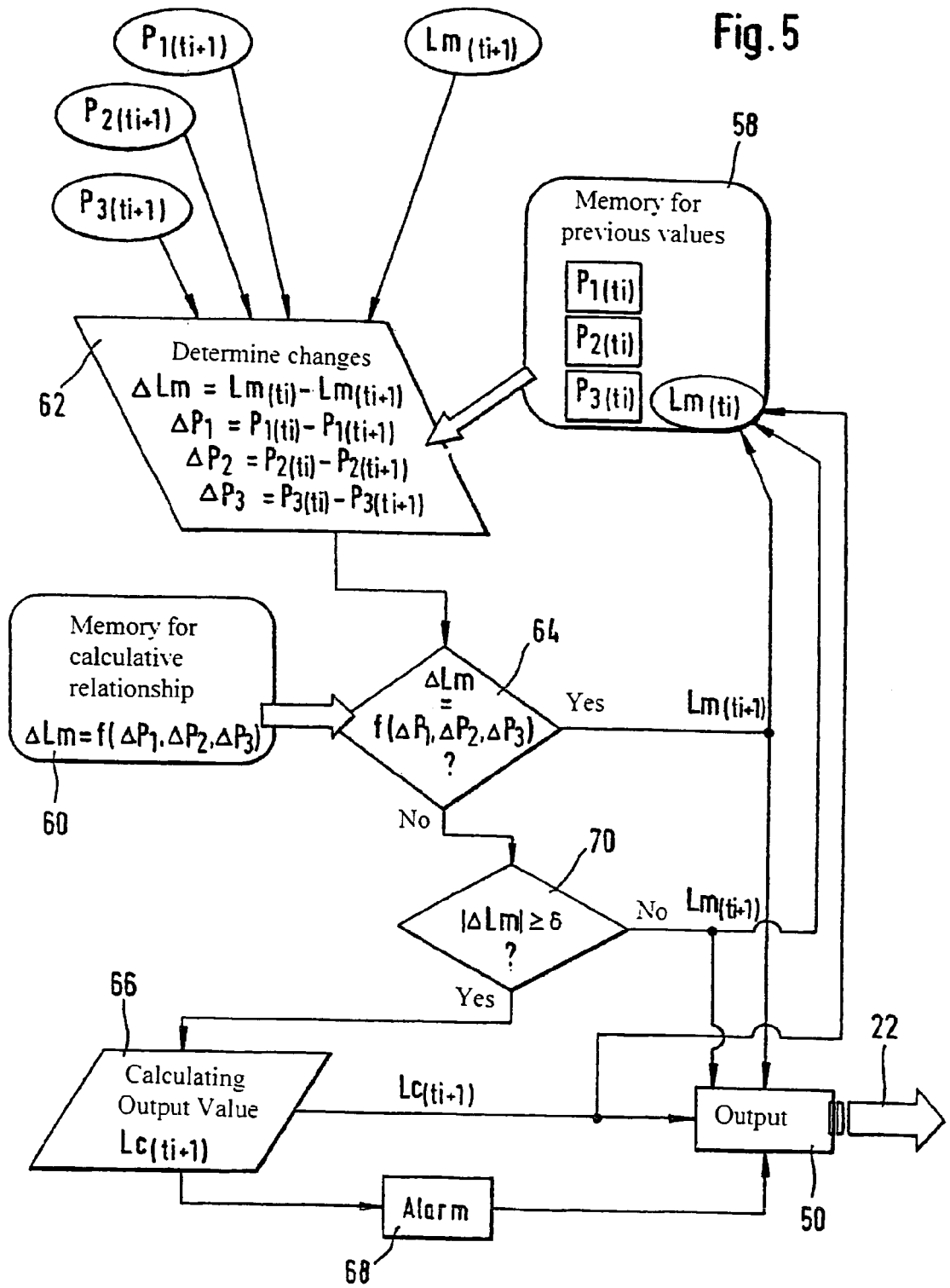
FIG. 5: is a flow diagram of a preferred second embodiment of a method for evaluating, error-blanking and -compensation according to the invention.

FIG. 5 illustrates by flow diagram another preferred embodiment of the method of the invention for evaluation, error-blanking and -compensation according to the invention. This embodiment is similar to that described above with respect to FIG. 4 in many components and method steps. Also in FIG. 5, by way of example, a time interval from a running measurement operation is selected for two, arbitrary per se, points in time, $t_i$ und $t_{i+1}$, one following the other. As in the case of the method illustrated in FIG. 4, a determination 62 of particular changes $\Delta Lm=Lm_{(ti)}-Lm_{(ti+1)}$ and $\Delta P_1$, $\Delta P_2$, $\Delta P_3$ takes place, using the measured values $P_{1(ti)}$, $P_{2(ti)}$, $P_{3(ti)}$ and $Lm_{(ti)}$ (or $Lc_{(ti)}$ in the case of an interference) for the time $t_i$, and the measured values $P_{1(ti+1)}$, $P_{2(ti+1)}$, $P_{3(ti+1)}$ and $Lm_{(ti+1)}$ from the time $t_{i+1}$. Likewise, also here it is tested, in a comparison 64, whether the change of the radiometric, measured value $\Delta Lm=Lm_{(ti)}-Lm_{(ti+1)}$ corresponds, or not, i.e. whether an interference is present, or not, to the changes $\Delta P_1$, $\Delta P_2$, $\Delta P_3$, registered in the corresponding time interval, of the process parameters in terms of the calculate relationship $\Delta Lm=f(\Delta P_1,\Delta P_2,\Delta P_3)$ read out of the memory 60.

In case not interference is ascertained, then, as already explained above, the process variable $L_{(ti+1)}$ belonging to the radiometric, measured value $Lm_{(ti+1)}$ is formed and issued via the output 50 onto the bus 22.

In case, however, an interference is ascertained, then, departing from the method of FIG. 4, a review 70 is performed, whether it is tested whether the change of the radiometric, measured value $\Delta Lm$ is smaller in size than a deviation $\delta$ from the calculate relationship $\Delta Lm=f(\Delta P_1,\Delta P_2,\Delta P_3)$ predetermined previously as maximally allowable. If the change of the radiometric, measured value $\Delta Lm$ is smaller than $\delta$ and it is thus still within a tolerable range of variance, the actually measured, radiometric, measured value $Lm_{(ti+1)}$ is considered to be acceptable. As described above, the process variable $L_{(ti+1)}$ belonging to the radiometric, measured value $Lm_{(ti+1)}$ is then formed and issued via the output 50 onto the bus 22.

In the case, where $|\Delta Lm| \geqq \delta$ and the change of the radiometric, measured value $\Delta Lm$ consequently deviates in size from the calculative relationship $\Delta Lm=f(\Delta P_1,\Delta P_2,\Delta P_3)$ by more than is permitted, an interference is assumed. As described above, the known calculative relationship $\Delta Lm=f(\Delta P_1,\Delta P_2,\Delta P_3)$ is then used to perform a calculation 66 for the time period $t_i$ to $t_{i+1}$ under consideration, in order to deliver for the time $t_{i+1}$ a calculated measurement $L_{(t+1)}$. In addition, the associated process variable $L_{(ti+1)}$ is determined and, together with an additional signal 68 indicating an interference, issued onto the bus 22 connected with the process control system.

Corresponding to the method of FIG. 4, in the method of FIG. 5 also, the particular value placed at the output 44, be it the calculated radiometric measurement $Lc_{(ti+1)}$ in the case of an interference or the actually-measured measured value $Lm_{(ti+1)}$, is loaded into the memory 58, where it is available for the following measuring time $t_{i+2}$ as a reference value for determining the change $\Delta Lm=Lc_{(ti+1)}-Lm_{(ti+2)}$, or $\Delta Lm=Lm_{(ti+1)}-Lm_{(ti+2)}$, for a following time period $t_{i+1}$ to $t_{i+2}$.

Figure 6:
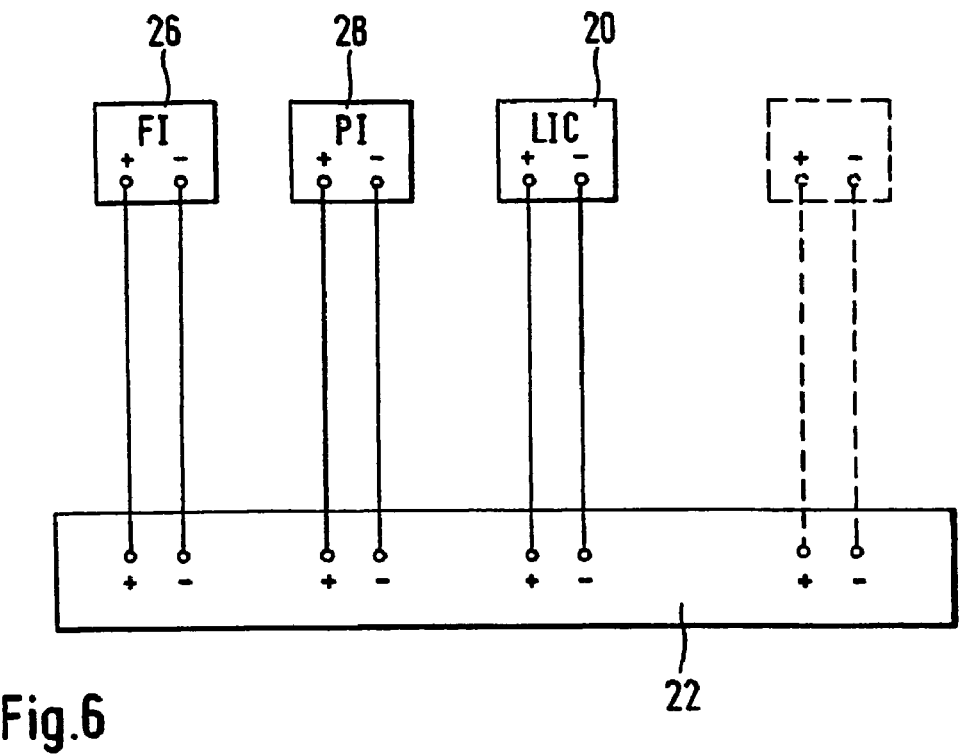
FIG. 6: is a schematic drawing of a conventional connecting, to a process control system, of a radiometric measuring system and other measuring devices serving for registering other process parameters.

In order to illustrate the simple manner in which the device of the invention can be integrated as a retrofit into existing, already-installed, process measurement equipment, FIG. 6 schematically depicts a conventional connecting to a process control system of a radiometric measuring system and other measuring instruments serving to register other, non-radiometrically registered process parameters. In doing so, then already shown by way of example in FIG. 1 is assumed for purposes of simplification (see, in this connection, FIG. 1 and the corresponding description). As shown by FIG. 6, usually the evaluation electronics 20 of the radiometric measuring system 14, the flow measuring device 26 and the pressure measuring 28 are connected directly to the bus 22. The hookup itself is shown in FIG. 6 for a usual, so-called two-wire system, for example according to the so-called HART Communication Foundation.

Figure 7:
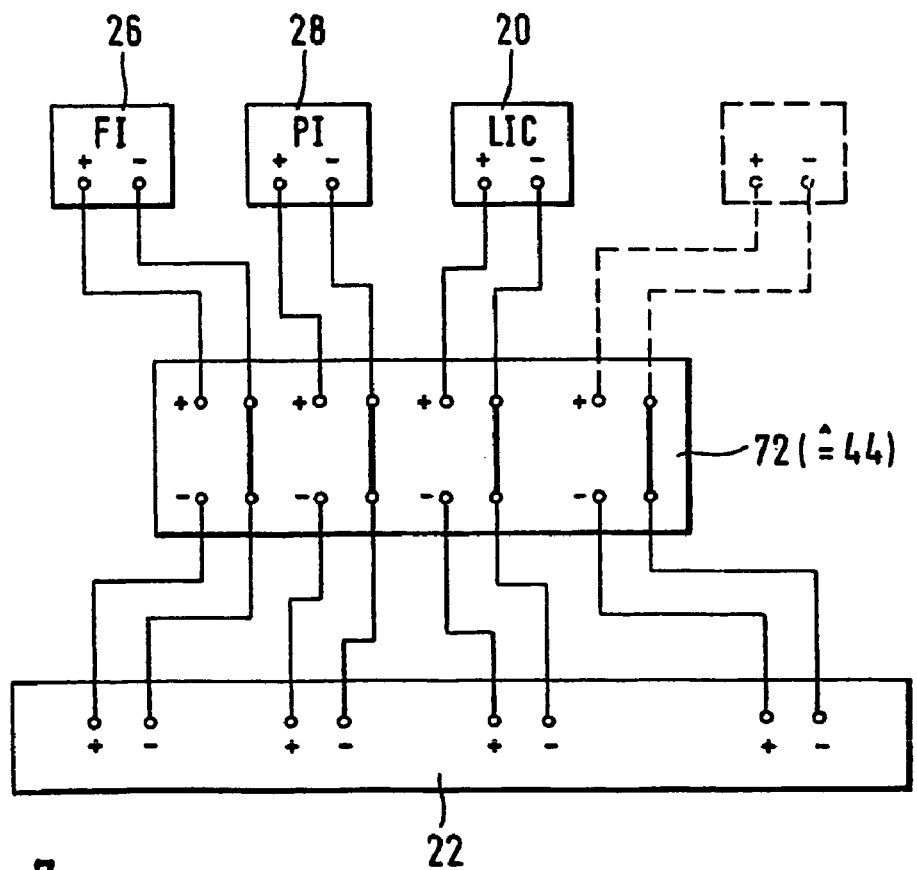
FIG. 7: is a schematic drawing of a connecting of a radiometric fill level measuring system, and other measuring systems for registering other process parameters, to a process control system, with the interposition of a device for error-blanking and -compensation according to the invention.

If now, by way of example, the device 44 of the invention for error-blanking and -compensation shown in FIG. 3 is supplied in the form of a retrofit-kit 72 (see, in this connection, FIG. 3 and the description belonging thereto), such retrofit-kit 72 can, as shown in FIG. 7, be connected, in the case of the equipment for process measurements of FIG. 6, between the bus 22 and the measuring devices 14, respectively 20, 26 and 28. The retrofit-kit includes preferably a housing (not shown) and, accommodated therein, the same modules and components as possessed by the device of FIG. 3 for error-blanking and -compensation. The hookup of the inputs and outputs occurs, in the case of a two-wire system, according to the so-called HART Communication Foundation in the manner shown in FIG. 7.

What is claimed is:

1. A method for error-blanking and -compensation of interference signals originating from gammagraphy in a radiometric measuring system, wherein a process variable $L_{(t)}$ is determined by means of a radioactive radiator and a detector, which method comprises the steps of:

determining the change $\Delta Lm=Lm_{(ti)}-Lm_{(ti+1)}$ for two, arbitrary per se, time $t_i$ and $t_{i+1}$, between two radiometric, measured values $Lm_{(ti)}$ and $Lm_{(ti+1)}$ registered by the detector at these times and, by means of a predetermined, calculative relationship $\Delta Lm=f(\Delta P_1)$, comparing said change with a change $\Delta P_1=P_{1(ti+1-\tau)}$ of a first, non-radiometrically measured process parameter, registered in the corresponding time interval; assuming that no interference of the radiometric measuring system is present in case the change $\Delta Lm=Lm_{(ti)}-Lm_{(ti+1)}$ of the radiometric, measured value $Lm_{(t)}$ corresponds to a previous change $\Delta P_1=P_{1(ti-\tau)}-P_{1(ti+1-\tau)}$ of the first, non-radiometrically measured process parameter in the corresponding time interval and to the calculative relationship $\Delta Lm=f(\Delta P_1)$, wherein, from the last-measured, radiometric, measured value $Lm_{(n+1)}$, the associated process variable $L_{(ti+1)}$ is determined and issued onto a bus connected with a process control system, without an additional signal indicating an interference; and assuming that an interference of the radiometric system is present in case the change $\Delta Lm=Lm_{(ti)}-Lm_{(ti+1)}$ of the radiometric, measured value $Lm_{(t)}$ does not correspond to a previous change $\Delta P_1=P_{1(ti-\tau)}-P_{1(ti+1-\tau)}$ of the first, non-radiometrically measured process parameter $P_1=P_{1(t-\tau)}$ in the corresponding time interval and to the calculative relationship $\Delta Lm=f(\Delta P_1)$, wherein:

based on the previous change $\Delta P_1=P_{1(ti-\tau)}-P_{1(ti+1-\tau)}$ of the first process parameter $P_1$, a radiometric measurement $Lc_{(t+1)}$ is calculated, by means of the recorded, calculative relationship $\Delta Lm=f(\Delta P_1)$, for the time $t_{i+1}$;

from the calculated, radiometric measurement $Lc_{(ti+1)}$, the associated process variable $L_{(ti+1)}$ is determined and issued onto the bus connected with the process control system, together with an additional, interference-indicating signal; and in a subsequent recording, at a time $t_{i+2}$, of the change $\Delta P_1=P_{1(ti+1-\tau)}-P_{1(ti+2-\tau)}$ of the first, non-radiometrically measured, process parameter and of the measuring of the radiometric, measured value $Lm_{(ti+2)}$, the latter is used together with the calculated radiometric measurement $Lc_{(ti+1)}$ to determine the change $\Delta Lm=Lc_{(ti+1)}-Lm_{(ti+2)}$ and this is referenced for determining whether an interference of the radiometric measuring system is still present.

2. The method as claimed in claim 1, wherein the following steps are performed before start-up of the radiometric measuring system;

identifying, for a measured value $Lm_{(t)}$ measured by the detector of the radiometric measuring system, at least one, non-radiometrically measured and likewise monitored, first process parameter $P_1=P_{1(t-\tau)}$, whose change $\Delta P_1=P_{1(ti-\tau)}-P_{1(ti+1-\tau)}$ leads, for arbitrary times $t_{j-\tau}$ and $t_{j+1-\tau}$, with delay by a possible delay time $\tau$, which can even be $\tau+0$, to a change $\Delta Lm=Lm_{(ij)}-Lm_{(ij+1)}$ of the radiometric, measured value $Lm_{(t)}$; and formulating and storing a calculative relationship $\Delta Lm=f(\Delta P_1)$ from changes $\Delta Lm$ of the radiometric, measured value $Lm_{(t)}$ determined at different operating and process conditions and at different times $t_i$ and resulting from changes $\Delta P_1$ of the non-radiometrically measured, first process parameter.

3. The method as claimed in claim 1, wherein:

prior to issue of the signal indicating the interference of the radiometric measuring system, it is ascertained whether the change $\Delta Lm$ of the radiometric, measured value is smaller in size than a change $\delta$ previously predetermined as maximally allowable from the calculative relationship $\Delta Lm=f(\Delta P_1)$; and only in the case where $|\Delta Lm| \geqq \delta$ is the signal indicating the interference of the radiometric measurement signal issued onto the bus.

4. The method as claimed in claim 1, wherein:

the measured value $Lm_{(t)}$ measured by the detector of the radiometric measuring system can be a measure for a fill level of a medium in a container, a density of such a medium in a container, or an interface of at least two phases of one or more media in a container or pipe.

5. The method as claimed in claim 4, wherein:

the first, non-radiometrically measured, process parameter $P_1$ is one of:

a pressure in the interior of the container or in a pipe connected with the interior of the container, a temperature in the interior of the container or in a pipe connected with the interior of the container, and a flow rate of a medium in a pipe connected with the interior of the container.

6. The method as claimed in claim 5, wherein:

a plurality of process parameters $P_k(k=1, 2, \ldots)$ are monitored, whose change $\Delta P_k=P_{k(tj-\tau k)}-P_{k(tj+1-\tau k)}$ for arbitrary times $t_{j-\tau k}$ and $t_{j+1-\tau k}$ leads, delayed by a possible delay time $\tau k$, which can also be $\tau k+0$, to change $\Delta Lm=Lm_{(tj)}-Lm_{(tj+1)}$ of the radiometric, measured value $Lm_{(t)}$;

on the basis of measurements of different operational and process conditions, a calculative representation of the dependence of the change of the radiometric, measured value $Lm_{(t)}$ on a change of each separate process parameter, or a plurality of the process parameters, $P_k$ is formulated to $\Delta Lm=f(\Delta P_1, \Delta P_2, \ldots)$; and during operation, it is examined by means of the calculatively recorded relationship $\Delta Lm=f(\Delta P_1, \Delta P_2, \ldots)$, whether an interference of the radiometric measuring system is present.

7. A device for error-blanking and -compensation of gammagraphy-caused interference signals in a radiometric measuring system with a radioactive radiator and a detector, which device includes:

an input for measured values $Lm_{(t)}$ measured by the detector for a process variable $L_{(t)}$, an input for at least one non-radiometrically measured and likewise monitored, first process parameter $P_1=P_{1(t-\tau)}$, whose change leads to a change $\Delta Lm=Lm_{(tj)}-Lm_{(tj+1)}$ of the radiometric measured value $Lm_{(t)}$ delayed by a possible delay time $\tau k$, which can also be $\tau k=0$;

an output, which is connected with a process control system, and an evaluation and error compensation facility, which:

determines during operation the change $\Delta Lm=Lm_{(ti)}-Lm_{(ti+1)}$ of the radiometric, measured values $Lm_{(ti)}$ und $Lm_{(ti+1)}$ registered by the detector at two, arbitrary per se, times $t_i$ and $t_{i+1}$ following one after the other, and, by means of the calculative relationship $\Delta Lm=f(\Delta P_1)$, compares such with a change $\Delta P_1=P_{1(ti-\tau)}-P_{1(ti+1-\tau)}$ of the first, non-radiometrically measured process parameter $P_1=P_{1(t-\tau)}$;

in case the change $\Delta Lm=Lm_{(ti)}-Lm_{(ti+1)}$ of the radiometric, measured value $Lm_{(t)}$ corresponds to a previous change $\Delta P_1=P_{1(ti-\tau)}-P_{1(ti+1-\tau)}$ of the first, non-radiometrically measured process parameter in the corresponding time interval and to a predetermined, calculative relationship $\Delta Lm=f(\Delta P_1)$, determines the associated process variable $L_{(ti+1)}$ from the last, measured, radiometric, measured value $Lm_{(ti+1)}$ and issues this variable to the output and onto a bus connected with a process control system, without an additional signal indicating an interference; and in case the change $\Delta Lm=Lm_{(ti)}-Lm_{(ti+1)}$ of the radiometric, measured value $Lm_{(t)}$ does not correspond to a previous change $\Delta P_1=P_{1(ti-\tau)}-P_{1(ti+-\tau)}$ of the first, non-radiometrically measured process parameter in the corresponding time interval and to a predetermined, calculative relationship $\Delta Lm=f(\Delta P_1)$, recognizes an interference of the radiometric measuring system, wherein:

based on the previous change $\Delta P_1=P_{1(ti-\tau)}-P_{1(ti+1-\tau)}$ of the first process parameter $P_1$, a radiometric measurement $Lc_{(t+1)}$ is calculated by means of the recorded, calculative relationship $\Delta Lm=f(\Delta P_1)$ for the time $t_{i+1}$;

the associated process variable $\overline{L}_{(ti+1)}$ is determined from the calculated radiometric measurement $Lc_{(ti+1)}$ and this variable is issued, with an additional signal indicating the interference, onto the output and onto the bus connected with the process control system; and in a subsequent, at a time $t_{i+2}$, registering of the change $\Delta P_1=P_{1(ti+1-\tau)}-P_{t(ti+2-\tau)}$ of the first, non-radiometrically measured process parameter and the measuring of the radiometric, measured value $Lm_{(ti+2)}$, the change $\Delta Lm=Lc_{(ti+1)}-Lm_{(ti+2)}$ is determined from this radiometric, measured value and the calculated radiometric measurement $Lc_{(ti+1)}$, in order to ascertain whether an interference of the radiometric measuring system is still present.

8. The device as claimed in claim 7, wherein:

before issue of the signal indicating the interference of the radiometric measuring system, it is examined, whether the change $\Delta Lm$ of the radiometric, measured value is smaller than a change $\delta=|\Delta Lm_{max}|$ previously determined as maximally allowable; and the signal indicating the interference of the radiometric measuring signal is issued onto the bus only in the case, where $\Delta Lm \geq \delta$.

9. The device as claimed in claim 7, wherein:

the measured value $Lm_{(t)}$ measured by the detector of the radiometric measuring system can be a measure for a fill level of a medium in a container, a density of such a medium in a container, or an interface of at least two phases of one or more media in a container or pipe.

10. The device as claimed in claim 9, wherein:

the first, non-radiometrically measured, process parameter $P_1$ is one of:

a pressure in the interior of the container or in a pipe connected with the interior of the container, a temperature in the interior of the container or in a pipe connected with the interior of the container, and a flow rate of a medium in a medium in a pipe connected with the interior of the container.

11. The device as claimed in claim 9, onto whose input a plurality of process parameters $P_k$ ($k=1, 2, \ldots$) are issued, whose change $\Delta P_k=P_{k(tj-\tau k)}-P_{k(tj+1-\tau k)}$ for arbitrary times $t_{j-\tau k}$ and $t_{j+1-\tau k}$ leads, delayed by a possible delay time $\tau k$, which can also be $\tau k=0$, to change $\Delta Lm=Lm_{(tj)}-Lm_{(tj+1)}$ of the radiometric, measured value $Lm_{(t)}$; wherein:

during operation of the evaluation and error-compensation facility it is examined by means of a predetermined, calculatively recorded relationship $\Delta Lm=f(\Delta P_1, \Delta P_2, \ldots)$, whether an interference of the radiometric measuring system is present.

12. The device as claimed in claim 7, wherein:

the device is part of an evaluation electronics assigned to the radiometric measuring system.

13. The device as claimed in claim 7, further including:

a housing which is independent of the detector of the radiometric measuring system, in which the device is accommodated.

14. The device as claimed in claim 7, wherein:

the device is placed as a retrofit kit between the measuring system and the process control system of an already installed radiometric measuring system.

15. The device as claimed in claim 7, wherein:

the calculative relationship $\Delta Lm=f(\Delta P_1, \Delta P_2, \ldots)$ for representing the dependence of the change of the radiometric, measured value $Lm_{(t)}$ on a change of each or a plurality of the non-radiometrically-won process parameters $P_k$ is obtained on the basis of measurements at various operational and process conditions.

* * * * *